United States Patent [19]

Bessman

[11] Patent Number: 5,057,090
[45] Date of Patent: Oct. 15, 1991

[54] DRIP METERING APPARATUS WITH SELECTABLE DROP SIZES AND COUPLING ARRANGEMENT THEREIN

[76] Inventor: Edward S. Bessman, 929 Rustling Oaks Dr., Millersville, Md. 21108

[21] Appl. No.: 536,348

[22] Filed: Jun. 7, 1990

[51] Int. Cl.$^5$ .............................................. A61M 5/00
[52] U.S. Cl. ...................................... 604/251; 604/51
[58] Field of Search ................ 604/251, 51, 126, 252, 604/253, 254, 122, 246

[56] References Cited

U.S. PATENT DOCUMENTS

| | | | |
|---|---|---|---|
| 2,648,333 | 8/1953 | Cutter . | |
| 2,969,063 | 1/1961 | Broman . | |
| 3,022,784 | 2/1962 | Nuffer . | |
| 3,807,397 | 4/1974 | Noiles . | |
| 3,848,634 | 11/1974 | Noiles | 137/601 |
| 4,065,093 | 12/1977 | Phillips | 251/6 |
| 4,186,740 | 2/1980 | Guerra | 604/51 X |
| 4,312,342 | 1/1982 | Chittenden | 604/51 X |
| 4,317,473 | 3/1982 | Gaydos | 138/45 |
| 4,449,534 | 5/1984 | Leibinsohn | 604/51 |
| 4,694,856 | 9/1987 | Leibinsohn | 137/555 |
| 4,781,698 | 11/1988 | Parren | 604/246 |
| 4,802,650 | 2/1989 | Stricker | 251/117 |
| 4,842,588 | 6/1989 | Jones | 604/251 X |
| 4,952,210 | 8/1990 | Alchas | 604/251 |

Primary Examiner—John D. Yasko
Attorney, Agent, or Firm—Shapiro and Shapiro

[57] ABSTRACT

A drip metering apparatus, as for parenteral liquid infusion, includes a coupling arrangement providing multiple passageways from a liquid supply connector to a drip chamber. The passageways lead from the supply connector to respective drop-forming outlets, with the outlets of the different passageways being dimensioned to form different drop sizes and disposed to introduce the respective drops into an upper region of the drip chamber. In a preferred embodiment, the passageways are coaxial with one another and with the drip chamber, with the outer passageway being bounded in part by a resiliently flexible, relatively large diameter outer tube and the inner passageway being bounded by a relatively rigid, relatively small diameter inner tube. The relative flow resistances through the two tubes are such that with a common inlet flow to the tubes and both tubes open, substantially the entire flow follows the outer tube so that the rate of small drop formation is negligible in comparison with the rate of large drop formation. Thus, selection between the two drop sizes may be made by pinching the outer tube shut against the inner tube (small drops) or leaving the outer tube open (large drops).

48 Claims, 3 Drawing Sheets

DRIP METERING APPARATUS WITH SELECTABLE DROP SIZES AND COUPLING ARRANGEMENT THEREIN

BACKGROUND OF THE INVENTION

This invention relates to liquid metering apparatus, and is more particularly concerned with a drip metering apparatus capable of producing different drop sizes selectively. The invention is also concerned with a coupling arrangement which may be attached to a drip meter for converting from single to multiple drop-size-producing capability.

The present invention has been devised with a particular view toward overcoming certain disadvantages of conventional parenteral (e.g., intravenous) liquid infusion systems, and accordingly will be described in this context. However, it is to be understood that the basic principles of the invention are not strictly limited to such applications.

In conventional parenteral liquid infusion systems, liquid to be administered to a patient is ordinarily metered through an apparatus comprising a transparent drip chamber which is connected through resilient plastic tubing between a liquid supply and a needle inserted into the patient. The drip chamber is capped by an inlet connector having a single drop-forming opening which forms the liquid received from the supply into drops of a predetermined volume and introduces the drops into the upper region of the drip chamber substantially on the drip chamber axis. The drops fall through the upper region to a reservoir at the bottom of the drip chamber, from which the liquid is conveyed to the patient. The volumetric flow rate to the patient (i.e., the infusion rate), and thus the rate of drop formation, is controlled by a flow regulating device, such as an adjustable clamp mounted on the flexible tubing beyond the drip chamber outlet. By monitoring the rate of drop formation— for example, visually or with a photo-electric drop rate monitor—attending personnel can determine the infusion rate.

The applicability of an infusion system such as just described is determined primarily by its rated drop size. Treatment situations requiring high infusion rates (e.g., resuscitating a patient from shock) or high viscosity liquids (e.g., plasma expanders or blood products) dictate the use of larger drops. Conversely, situations requiring low, precisely controlled infusion rates of lower viscosity liquids (e.g., treatment of pediatric patients or infusion of potent pharmaceutical solutions) dictate the use of smaller drops. In view of these distinctly different requirements, conventional parenteral liquid drip metering equipment is manufactured to produce either large drops (usually about 1/20 ml. per drop) or small drops (usually about 1/60 ml. per drop), and attending medical personnel must select equipment rated appropriately to the task at hand.

The limited applicability of single-drop-size infusion systems presents a number of problems. For example, in emergency situations requiring immediate intravenous access, the initial selection between differently rated infusion sets must often be based on only partial information about the patient's condition. If, as is often the case, further information should prove the initial selection to be inappropriate, the equipment must be changed. This wastes precious time and increases the risk of infection to the patient. Additionally, in emergency and non-emergency situations alike, routine medical procedure or changes in the condition of the patient may require the administration of a liquid incompatible with a previously selected infusion set. Again, the equipment must be changed, wasting time and increasing the risk of infection to the patient.

It is thus apparent that there is a need for a practically designed drip metering apparatus capable of producing multiple drop sizes on a selective basis. Such an apparatus would be advantageous not only in terms of obviating the aforementioned problems, but also in terms of more efficient equipment utilization, by (in many cases) reducing the amount of equipment required to treat individual patients. Moreover, such an apparatus would relieve medical facilities from the burden of maintaining separate inventories of correspondingly rated single-drop-size devices.

In one recent proposal which attempts to address this need, U.S. Pat. No. 4,781,698 ("the '698 patent") discloses a specially designed drip chamber incorporating an adjustable drop forming mechanism. The drip chamber includes relatively rotatable upper and lower sections, the upper section having a discharge opening at its base and the lower section having a plurality of drop tubes mounted at circumferentially spaced eccentric positions on a top plate thereof. The drop tubes, which have different cross-sectional areas for producing different drop sizes, may be brought selectively into registration with the discharge opening by relative rotation of the upper and lower drip chamber sections.

The incorporation of an adjustable drop-forming mechanism into the drip chamber as proposed in the '698 patent creates several problems. First, the manufacturing process becomes more complex and expensive due to the need for multiple castings, moving parts, and precision surfaces sealed by O-rings. Second, the eccentric location of the drop-forming tubes renders the device incompatible with conventional photo-electric drop counters which require that drops be introduced substantially on the axis of the drip chamber. Third, the eccentric geometry renders the device more sensitive to position, as even small deviations from vertical (which are quite common, for example, during transport of emergency patients to the hospital) result in the drops impinging on the side of the drip chamber, making even visual counting difficult.

SUMMARY OF THE INVENTION

The present invention addresses the matter of multiple drop-size formation from a different point of view, with a principal focus not on the structure of the drip chamber per se, but rather on the arrangement by which liquid is conveyed from the supply to the drip chamber. From a general perspective, the invention embraces the use of multiple passageways uniquely cooperatively arranged (as described hereinafter), preferably at both the inlet and outlet ends thereof, for conveying liquid to a drip chamber.

In an especially preferred implementation to be described, the invention provides a drip metering apparatus with selectable drop size capability, but without the structural complexities and concomitant disadvantages of the device of the aforementioned '698 patent. As will be seen, this preferred apparatus is of relatively simple construction, easy to manufacture, readily switched between large and small drop sizes, compatible with conventional photo-electric drop counters, and has a position sensitivity on par with current single-drop-size apparatus.

According to one of its basic aspects, however, the invention provides drip metering apparatus comprising a drip chamber, supply connector means for connection to a liquid supply, and means coupling the drip chamber to the supply connector means for conveying the liquid to an upper region of the drip chamber and introducing the liquid into the drip chamber upper region in the form of drops. The coupling means defines first and second passageways having respective inlet ends arranged to confront a common flow of the liquid from the supply connector means and respective drop-forming outlet ends disposed for introducing drops of the liquid into an upper region of the drip chamber, the drop-forming outlet end of the first passageway being dimensioned to form relatively large drops, and the drop-forming outlet end of the second passageway being dimensioned to form relatively small drops. The relative resistances to flow through the two passageways are such that when both of the passageways are open, the rate of drop formation at the outlet end of the second passageway is negligible in comparison with the rate of drop formation at the outlet end of the first passageway, whereby selection between the small and large drops may be made by blocking the first passageway or leaving the first passageway open in accordance with the desired drop size.

According to another of its basic aspects, the invention provides drip metering apparatus comprising a drip chamber, supply connector means for connection to a liquid supply, and means coupling the drip chamber to the supply connector means for conveying the liquid to an upper region of the drip chamber and introducing the liquid into the drip chamber upper region in the form of drops. The coupling means defines first and second passageways having respective inlet ends arranged to receive liquid from the supply connector means and respective drop-forming outlet ends disposed for introducing drops of the liquid into an upper region of the drip chamber, with the drop-forming outlet end of the first passageway being dimensioned to form relatively large drops, and the drop-forming outlet end of the second passageway being dimensioned to form relatively small drops and disposed such that liquid flowing therethrough to the upper region of the drip chamber passes through the drop-forming outlet end of the first passageway without interference of the drop-forming outlet end of the first passageway with the small drops.

According to yet another of its basic aspects, the invention provides drip metering apparatus comprising a drip chamber supply connector means for connection to a supply of liquid, and means coupling the drip chamber to the supply connector means for conveying the liquid to an upper region of the drip chamber and introducing the liquid into the drip chamber upper region in the form of drops. The coupling means defines an inner passageway extending within an outer passageway, with the passageways having respective inlet ends arranged to confront a common flow of liquid from the supply connector means and respective drop-forming outlet ends disposed for introducing drops of the liquid into an upper region of the drip chamber, and with the drop-forming outlet end of the outer passageway being dimensioned to form relatively large drops, and the drop-forming outlet end of the inner passageway being dimensioned to form relatively small drops. Preferably, the relative resistances to flow through the inner and outer passageways are such that when both of the passageways are open, the rate of drop formation at the drop-forming outlet end of the inner passageway is negligible in comparison with the rate of drop formation at the drop-forming outlet end of the outer passageway, whereby selection between the small drops and the large drops may be made by blocking the outer passageway or leaving the outer passageway open in accordance with the desired drop size.

Still another basic aspect of the invention pertains to a coupling apparatus for use in converting a single-drop-size drip metering apparatus to multiple-drop-size capability, as will be discussed hereinafter.

BRIEF DESCRIPTION OF THE DRAWINGS

The above-noted and other aspects and advantages of the invention will be better understood upon consideration of the following detailed description taken in conjunction with the accompanying drawings, in which.

DETAILED DESCRIPTION OF THE INVENTION

Figure 1:
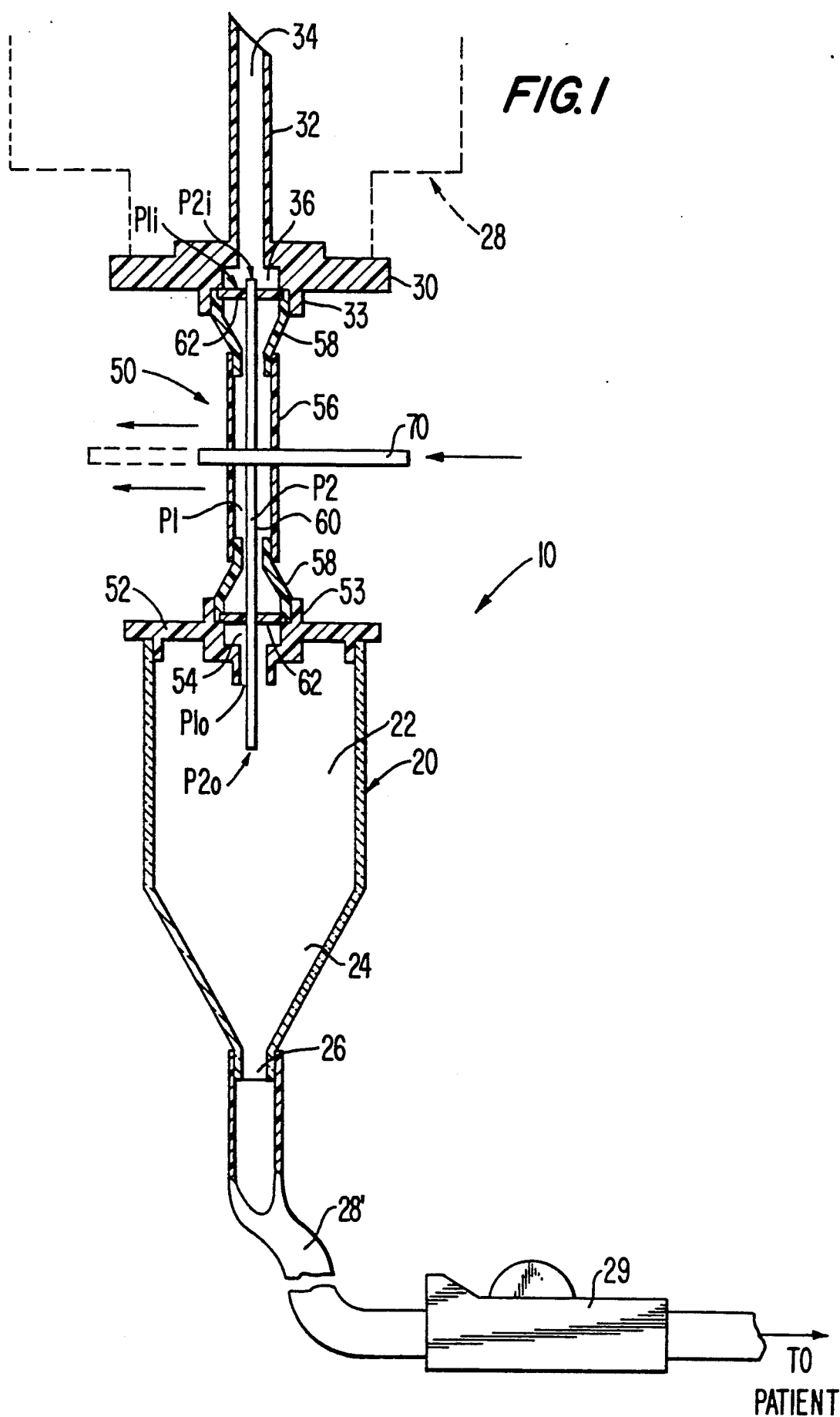
FIG. 1 is a diagrammatic side elevation, partly in section, showing a drip metering apparatus of the invention as applied in a parenteral liquid infusion system.

Referring now to the drawings, FIG. 1 illustrates a drip metering apparatus 10 in accordance with a preferred embodiment of the invention, as applied for parenteral infusion purposes. The apparatus 10 includes a drip chamber 20 having a cylindrical upper region 22 and a conical lower region 24 with an outlet 26 at its base. Drip chamber 20 is connectible to a supply of liquid, such as an intravenous liquid bag indicated diagrammatically at 28, through a supply connector 30 and a coupling arrangement 50 for conveying liquid from the supply connector to the drip chamber upper region 22. Supply connector 30 is basically similar to those commonly used in parenteral liquid infusion systems, being provided with a hollow spike 32 for insertion through a stopper of the liquid supply bag 28 to tap the liquid contained therein. An outlet passageway 34 of the supply connector extends through spike 32 and terminates at an outlet 36, to which the coupling arrangement is connected. As will be explained shortly, coupling arrangement 50 is designed to form both large volume drops and small volume drops and to enable the selective introduction of either drop size into the drip chamber upper region. The outlet 26 of the drip chamber is connectible to a patient through resilient flexible tubing 28', which leads to a needle (not shown) for insertion into the patient. In conventional fashion, tubing 28' passes through an adjustable regulator clamp 29 which controls the volumetric flow rate through the apparatus.

Figure 4:
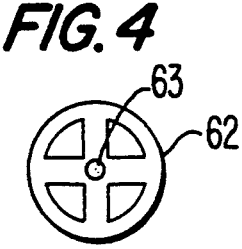
FIG. 4 is a plan view of a fenestrated disk used in the FIG. 1 apparatus for purposes described hereinafter.

In accordance with the present invention, coupling arrangement 50 defines two passageways for liquid flow to the drip chamber upper region 22, with each passageway being utilized for the purpose of forming a respective one of the two (small and large) drop sizes. In the form shown, a first passageway P1 is bounded by the wall of a bore 54 through an inlet connector 52 which fixedly caps drip chamber 20, a resiliently flexible tube 56, and a pair of annular adapters 58 respectively connecting opposite ends of tube 56 to corresponding cylindrical fittings 33 and 53 of supply connector 30 and drip chamber inlet connector 52. For simplicity of assembly, the adapters may be dimensioned to make a secure press fit with fittings 33 and 53 and with the ends of tube 56. A second passageway P2 is bounded by a relatively small diameter tube 60 which is supported substantially coaxially within tube 56 by a pair of fenestrated disks 62 mounted to inner peripheral recesses of the adapters 58, as shown in FIG. 1. FIG. 4 shows a preferred configuration of disks 62, the central hole 63 of course being provided for retainably receiving tube 60. Again for simplicity of assembly, disks 62 may be designed to make a secure press fit with adapters 58 and with tube 60.

For the purpose of forming the large volume (e.g., 1/20 ml.) drops, bore 54 of the inlet connector is provided with an appropriately dimensioned opening $P1_o$ which constitutes a drop-forming outlet end of passageway P1. Preferably, as shown in FIG. 1, drop-forming opening $P1_o$ is coaxial with drip chamber 20 (i.e., centered on the drip chamber vertical axis), such that drops formed by the opening fall into the drip chamber substantially on the drip chamber axis. The diameter (internal) of tube 60 is selected such that an outlet opening $P2_o$ of the tube, which also constitutes the outlet end of passageway P2, is appropriately dimensioned for the purpose of forming the small volume (e.g., 1/60 ml.) drops.

The relative positioning of the passageway outlet ends $P1_o$ and $P2_o$ constitutes a preferred implementation of an important aspect of the invention. Basically, the outlet $P2_o$ is arranged such that the liquid flowing therethrough enters the drip chamber 20 by way of outlet $P1_o$, but without interference of outlet $P1_o$ with the small drops. This allows for multiple drop-size-producing capability with a drip chamber inlet connector having only a single through-bore. In the illustrative arrangement, inner tube 60 is extended through the large drop outlet $P1_o$ to locate the small drop outlet $P2_o$ further into the drip chamber, thus precluding interfering contact of the outlet $P1_o$ with the small drops formed by outlet $P2_o$. Depending on the drop sizes involved in a particular case, however, the location of inner tube 60 toward the axis of outlet $P1_o$ without actually extending the inner tube therethrough may be sufficient to avoid such interference. Such an arrangement would be somewhat more position sensitive, though, since substantial deviations of the drip chamber from vertical could cause the small drops to fall against the walls of outlet $P1_o$, rather than through the outlet. Either arrangement is advantageous, however, in that the inlet connector to the drop chamber need only be formed with a single through-bore.

The inlet ends of passageways P1 and P2 are constituted respectively by the space $P1_i$ between the upper adapter 58 and the inner tube 60 (which space in this case is partially occupied by the upper fenestrated disk 62) and by an inlet end opening $P2_i$ of the inner tube itself. Since both of the inlets $P1_i$ and $P2_i$ thus confront the flow of liquid from the supply connector outlet passageway 34, the passageways P1 and P2 provide alternate flow paths from the supply connector outlet to the drip chamber upper region.

In accordance with another important aspect of the invention, the dimensions of passageways P1 and P2 are selected such the flow resistance through passageway P2 is very high relative the flow resistance through passageway P1. Specifically, the relative flow resistances of the passageways are such that when both passageways are open, substantially the entire liquid flow from supply connector outlet passageway 34 will follow passageway P1, whereby the rate of small drop formation at outlet $P2_o$ is negligible in comparison with the rate of large drop formation at outlet $P1_o$. Suitable passageway dimensions for any particular embodiment may readily be determined by one of ordinary skill in the art. In the illustrative embodiment, for example, outlet opening $P1_o$ may be about 2.8 mm. in diameter for producing 1/20 ml. drops, and the total length of passageway P1 may be about 50 mm., with tube 56 being about 30 mm. long and about 3 mm. in diameter (internal). Inner tube 60 may be about 0.56 mm. (20 gauge) in diameter (internal) for producing 1/60 ml. drops, and about 65 mm. long.

Figure 3A:
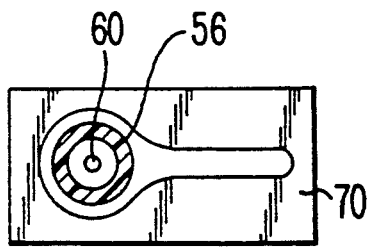
FIGS. 3A and 3B depict the operation of the clamp of FIG. 2.
Figure 3B:
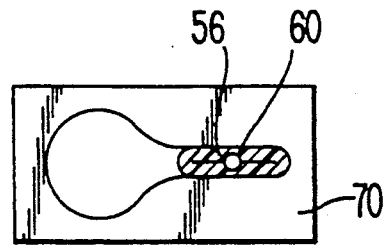
Figure 2:
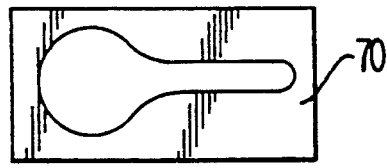
FIG. 2 is a plan view of a clamp used for drop-size selection in the apparatus of FIG. 1.

With relative flow resistances of the passageways as just described, selection between the two drop sizes may thus be accomplished simply by blocking or leaving open passageway P1. For this purpose, a two-position slide clamp 70 (better seen in FIG. 2) may be mounted about tube 56 for selectively pinching tube 56 shut against tube 60, which of course must have sufficient rigidity that it will not be pinched shut by the pinching force on tube 56. Blocking passageway P1, as by positioning clamp 70 as shown in FIG. 3B, restricts the liquid flow to passageway P2 and thus results in the formation of only small drops. Leaving passageway P1 open, as by positioning clamp 70 as shown in FIG. 3A, results in the almost exclusive formation of large drops due to the relative flow resistances of the passageways.

As will be readily apparent, the operation of the FIG. 1 apparatus is essentially the same as that of conventional parenteral infusion systems, except that the drop size (small or large) may be selected by the operator by adjusting clamp 70 as was just discussed.

Regarding materials of construction, drip chamber 20, connectors 30 and 52, and tubing 28' may all be made of plastics conventionally used for such components in parenteral infusion systems. Tube 56 may be made of the same material as tubing 28'. For example, both tubes may be conventional PVC intravenous tubing, although a softer material such as "Silastic" tubing may be preferred for tube 56 in order to assure tighter sealing against tube 60. Adapters 58 and disks 62 may be made of any plastic with suitable strength and rigidity, as may clamp 70. Tube 60 is preferably made of stainless steel to assure the necessary rigidity to withstand, without deformation, the pinching of tube 56 thereagainst.

Figure 5:
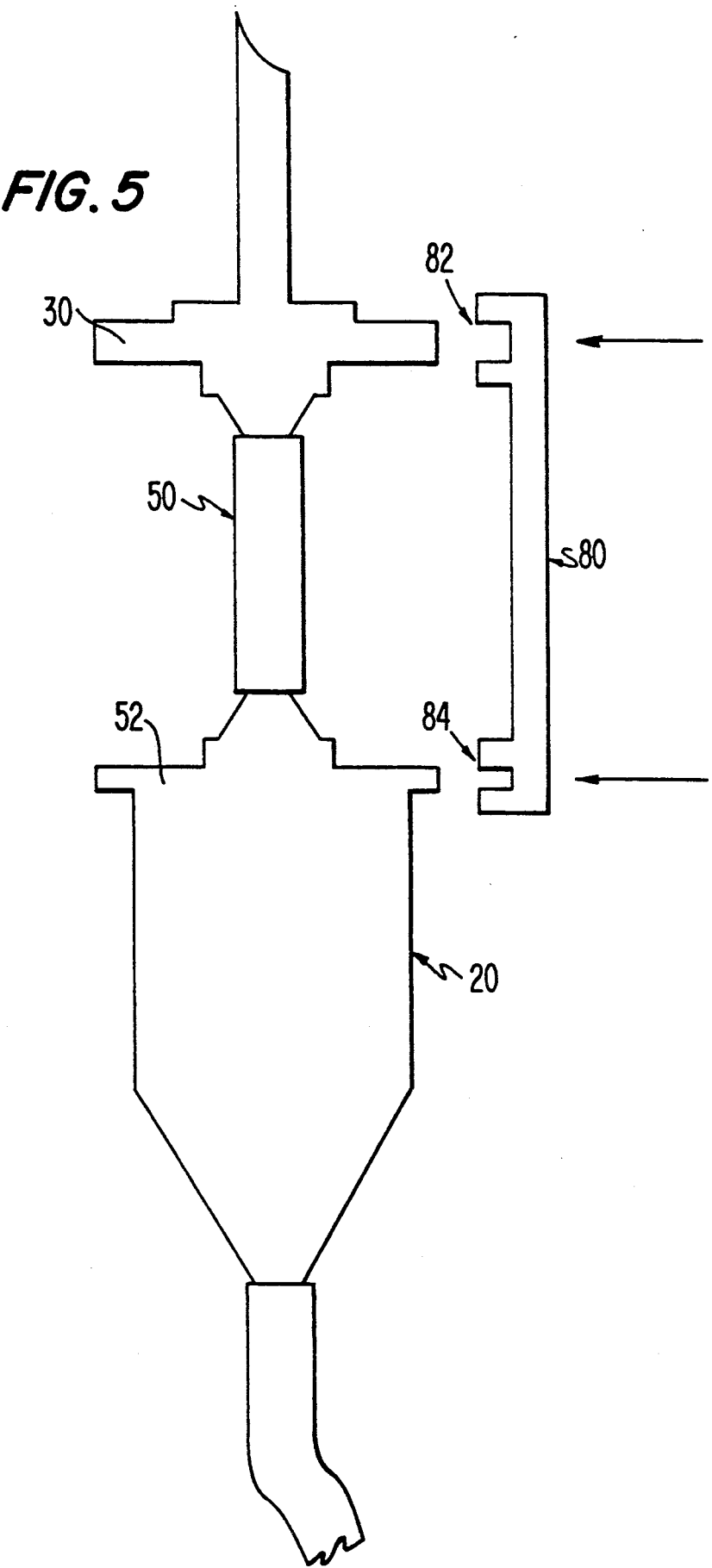
FIG. 5 is a diagrammatic side elevation showing a stabilizing arrangement which may be incorporated in the apparatus of FIG. 1.

FIG. 5 shows an arrangement for stabilizing the coupling between the supply connector and the drip chamber and, more specifically, for stabilizing the drip chamber 20 relative to the supply connector 30. In the apparatus of FIG. 1, there is some degree of stabilization provided by virtue of the rigid connection of inlet connector 52 to supply connector 30, successively through lower adapter 58, lower fenestrated disk 62, tube 60, upper fenestrated disk 62, and upper adapter 58. The rigidity of this connection, and therefore the stability of the coupling, depends largely on the rigidity and strength of tube 60. For field use in particular, where the apparatus may be subjected to abrupt movement and vibration (e.g., in emergency rescue situations and patient transport to the hospital), it is advantageous to provide a stabilizing arrangement such as shown in FIG. 5.

In the FIG. 5 arrangement, a rigid bar member 80 has jaw-like opposite ends 82, 84 which, as indicated by arrows in the drawing, are respectively fitted tightly over the peripheral flanges of the supply and inlet connectors 30 and 52 to provide a strong rigid connection directly between the connectors. This stabilizes the coupling arrangement 50 and avoids possible damage of tube 60, such as crimping or breakage due to bending moments under severe conditions of use.

Of course, the stabilizing arrangement may take various other forms. For example, the inlet and supply connectors and the stabilizing member (or members) could be formed as an integral, unitary structure—as by molding.

In practice of the invention for parenteral liquid infusion purposes, it is preferable as a matter of convenience that the subject drip metering apparatus be provided as a set, including drip chamber, connectors, tubes, etc. It will be apparent, however, that with appropriately designed connecting elements and inner tube supports (e.g., adapters and fenestrated disks), a coupling apparatus may be provided for converting almost any combination of drip chamber and supply and inlet connectors of conventional single drop-size design to multiple drop-size capability, by adding the smaller drop-size capability of the inner tube.

Although various passageway arrangements may be utilized in implementing the present invention, a coaxial passageway arrangement such as that of the above-described embodiment is especially preferred, because it combines the advantages of several aspects of the invention in a single embodiment. First, the passageway outlet arrangement provides multiple-drop-size producing capability with a drip chamber inlet connector having only a single through-bore. When the outlets ar also arranged coaxially with the drip chamber (or at least with the drip chamber upper region), there is the added benefit of full compatibility with conventional electronic drop counters—that is, compatibility with both drop sizes. Second, the passageway inlet arrangement, with both inlets confronting the supply connector outlet flow, is suitable for use of the earlier-described differential flow resistance principle, which enables drop size selection by simple control of the larger (outer passageway. Third, each of the inlet and outlet arrangements requires only a single connection to the associated connector (drip chamber inlet connector or supply connector) in order to couple the liquid supply to the drip chamber through both passageways.

While a preferred embodiment of the invention has been described herein, it will be apparent to those skilled in the art that the fundamental principles of the invention may be implemented in many different forms.

I claim as my invention:

1. Drip metering apparatus, comprising:
   a drip chamber,
   supply connector means for connection to a supply of liquid, and
   means coupling said drip chamber to said supply connector means for conveying said liquid to an upper region of said drip chamber and introducing said liquid into said upper region in the form of drops,
   said coupling means defining an inner passageway extending within an outer passageway, with said inner and outer passageways having respective inlet ends arranged to confront a common flow of said liquid from said supply connector means and respective drop-forming outlet ends disposed for introducing drops of said liquid into an upper region of said drip chamber, the drop-forming outlet end of said outer passageway being dimensioned to form relatively large volume drops, and the drop-forming outlet end of said inner passageway being dimensioned to form relatively small volume drops.

2. Drip metering apparatus according to claim 1, wherein the relative resistances to flow through said inner and outer passageways are such that when both of said passageways are open, the rate of drop formation at said drop-forming outlet end of said inner passageway is negligible in comparison with the rate of drop formation at said drop-forming outlet end of said outer passageway, whereby selection between said small volume drops and said large volume drops may be made by blocking said outer passageway or leaving said outer passageway open in accordance with the desired drop size.

3. Drip metering apparatus according to claim 2, wherein said coupling means includes a resiliently flexible outer tube of relatively large diameter bounding at least a portion of said outer passageway and an inner tube of relatively small diameter extending within said outer tube and bounding at least a portion of said inner passageway, said inner tube being sufficiently rigid relative to said outer tube that said outer tube may be pinched shut against said inner tube to block said outer passageway without blocking said inner tube.

4. Drip metering apparatus according to claim 3, further including clamp means mounted on said coupling means for pinching said outer tube shut against said inner tube.

5. Drip metering apparatus according to claim 3, wherein said inner passageway is substantially coaxial with said outer passageway.

6. Drip metering apparatus according to claim 5, wherein said inner and outer passageways are substantially coaxial with said upper region of said drip chamber.

7. Drip metering apparatus according to claim 3, wherein said drop-forming outlet end of said inner passageway is constituted by an end of said inner tube.

8. Drip metering apparatus according to claim 7, wherein said inner tube is substantially coaxial with said outer tube.

9. Drip metering apparatus according to claim 7, wherein said inner tube is substantially coaxial with said drop-forming outlet end of said outer passageway.

10. Drip metering apparatus according to claim 9, wherein said drop-forming outlet end of said outer passageway is substantially coaxial with said upper region of said drip chamber.

11. Drip metering apparatus according to claim 7, wherein said inner tube extends through said drop-forming outlet end of said first passageway into said upper region of said drip chamber.

12. Drip metering apparatus according to claim 11, wherein said drop-forming outlet end of said outer passageway is formed in an inlet connector mounted on said drip chamber.

13. Drip metering apparatus according to claim 12, wherein at least one end of said outer tube is connected to a corresponding one of said supply connector means and said inlet connector by an adapter.

14. Drip metering apparatus according to claim 13, wherein said inner tube is supported from said adapter by a fenestrated disk mounted to said adapter.

15. Drip metering apparatus according to claim 12, wherein said inner tube extends through said drop-forming outlet end of said outer passageway into said upper region of said drip chamber.

16. Drip metering apparatus according to claim 3, further including stabilizing means rigidly connecting said supply connector means and said drip chamber independently of said inner tube for stabilizing said coupling means.

17. Drip metering apparatus according to claim 16, wherein said stabilizing means includes a rigid bar member having opposite ends fixedly attached directly to said supply connector means and to an inlet connector mounted on said drip chamber, respectively.

18. Drip metering apparatus according to claim 3, including means connected to an outlet of said drip chamber for conveying said liquid to a patient for parenteral infusion purposes.

19. Drip metering apparatus, comprising:
a drip chamber,
supply connector means for connection to a liquid supply, and
means coupling said drip chamber to said supply connector means for conveying said liquid to an upper region of said drip chamber and introducing said liquid into said upper region in the form of drops,
said coupling means defining first and second passageways having respective inlet ends arranged to confront a common flow of said liquid from said supply connector means and respective drop-forming outlet ends disposed for introducing drops or said liquid into an upper region of said drip chamber, the drop-forming outlet end of said first passageway being dimensioned to form relatively large volume drops, and the drop-forming outlet end of said second passageway being dimensioned to form relatively small volume drops,
the relative resistances to flow through said first and second passageways being such that when both of said passageways are open, the rate of drop formation at said outlet end of said second passageway is negligible in comparison with the rate of drop formation at said outlet end of said first passageway, whereby selection between said s all volume drops and said large volume drops may be made by blocking said first passageway or leaving said first passageway open in accordance with the desired drop size.

20. Drip metering apparatus according to claim 19, further including means for selectively blocking and opening said first passageway.

21. Drip metering apparatus according to claim 19, wherein said coupling means includes a relatively large diameter first tube bounding at least portion of said first passageway and a relatively small diameter second tube bounding at least a portion of said second passageway.

22. Drip metering apparatus according to claim 21, wherein said first tube is resiliently flexible, and further including clamp means for pinching said first tube shut to block said first passageway.

23. Drip metering apparatus according to claim 22, wherein said second tube is surrounded by said first tube and sufficiently rigid relative to said first tube that said first tube may be pinched shut against said second tube by said clamp means without pinching shut said second tube.

24. Drip metering apparatus according to claim 21, wherein said drop-forming outlet end of said second passageway is constituted by an end of said second tube.

25. Drip metering apparatus according to claim 24, wherein said end of said second tube is disposed such that liquid flowing therethrough to said upper region of said drip chamber passes through said drop-forming outlet end of said first passageway without interference of said drop-forming outlet end of said first passageway with said small volume drops.

26. Drip metering apparatus according to claim 25, wherein said end of said second tube is extended through said drop-forming outlet end of said first passageway into said upper region of said drip chamber.

27. Drip metering apparatus according to claim 19, including means connected to an outlet of said drip chamber for conveying said liquid to a patient for parenteral infusion purposes.

28. Drip metering apparatus, comprising:
a drip chamber,
supply connector means for connection to a liquid supply, and
means coupling said drip chamber to said supply connector means for conveying said liquid to an upper region of said drip chamber and introducing said liquid into said upper region in the form of drops,
said coupling means defining first and second passageways having respective inlet ends arranged to receive said liquid from said supply connector means and respective drop-forming outlet ends disposed for introducing drops of said liquid into an upper region of said drip chamber, with said drop-forming outlet end of said first passageway being dimensioned to form relatively large volume drops, and said drop-forming outlet end of said second passageway being dimensioned to form relatively small volume drops and disposed such that liquid flowing therethrough to said upper region of said drip chamber passes through said drop-forming outlet end of said first passageway without interference of said drop-forming outlet end of said first passageway with said small volume drops.

29. Drip metering apparatus according to claim 28, wherein said second passageway is extended through said drop-forming outlet end of said first passageway such that said drop-forming outlet end of said second passageway is disposed in said upper region of said drip chamber.

30. Drip metering apparatus according to claim 28, wherein said drop-forming outlet end of said second passageway is substantially coaxial with said drop-forming outlet end of said first passageway.

31. Drip metering apparatus according to claim 30, wherein said drop-forming outlet ends of said first and second passageways are substantially coaxial with said upper region of said drip chamber.

32. Drip metering apparatus according to claim 28, wherein said coupling means includes a tube bounding at least a portion of said second passageway, and an end of said tube constitutes said drop-forming outlet end of said second passageway.

33. Drip metering apparatus according to claim 32, wherein said coupling means includes another tube surrounding the first-mentioned tube and bounding at least a portion of said first passageway.

34. Drip metering apparatus according to claim 33, wherein said another tube is connected to said drop-forming outlet end of said first passageway by an adapter, and said first-mentioned tube is supported from said adapter by a fenestrated disk.

35. Drip metering apparatus according to claim 33, wherein said another tube is resiliently flexible, and said first-mentioned tube is sufficiently rigid relative to said another tube that said another tube may be pinched shut thereagainst to block said first passageway without blocking said first-mentioned tube.

36. Drip metering apparatus according to claim 35, further including clamp means for pinching said another tube shut against said first-mentioned tube.

37. Drip metering apparatus, comprising:
a drip chamber;
supply connector means for connection to a supply of liquid, and
means coupling said drip chamber to said supply connector means for conveying said liquid to an upper region of said drip chamber and introducing said liquid into said upper region in the form of drops,
said coupling means including a pair of tubes arranged substantially coaxially one within the other,
the outer of said tubes being resiliently flexible and having an inlet end connected to an outlet of said supply connector means for confronting an outlet flow of said liquid and an outlet end connected to a drop-forming opening dimensioned to form relatively large volume drops of said liquid and disposed substantially coaxially with said upper region to introduce said drops into said upper region, of said tubes having an inlet end
the inner of said tubes having an inlet end arranged to confront said flow of said liquid and a drop-forming outlet end dimensioned to form relatively small volume drops of said liquid and disposed substantially coaxially with said upper region to introduce said small drops into said upper region,
said inner tube further being sufficiently rigid relative to said outer tube that said outer tube may be pinched shut against said inner tube without pinching shut said inner tube,
the relative resistances to flow through said tubes being such that when both of said tubes are open, the rate of drop formation at said drop-forming outlet of said inner tube is negligible in comparison with the rate of drop formation at said drop-forming opening, whereby selection between said small volume drops and said large volume drops may be made by pinching said outer tube shut or leaving said outer tube open in accordance with the desired drop size.

38. Drip metering apparatus according to claim 37, further including clamp means for pinching said outer tube shut against said inner tube.

39. Drip metering apparatus according to claim 37, wherein said outer tube is connected to said outlet of said supply connector means and to said drop-forming opening by adapters at its opposite ends.

40. Drip metering apparatus according to claim 39, wherein said coupling means includes means supporting said inner tube from said adapters.

41. Drip metering apparatus according to claim 39, wherein said supporting means comprises fenestrated disks.

42. Drip metering apparatus according to claim 37, further including stabilizing means rigidly connecting said supply connector means and said drip chamber independently of said inner tube for stabilizing said coupling means.

43. Drip metering apparatus according to claim 42, wherein said stabilizing means includes a rigid bar member having opposite ends fixedly attached directly to said supply connector means and to an inlet connector mounted on said drip chamber, respectively.

44. Drip metering apparatus according to claim 37, further comprising means connected to an outlet of said drip chamber for conveying said liquid to a patient for parenteral infusion purposes.

45. For use in a drip-metering apparatus including a drip chamber, an inlet connector with a drop-forming opening dimensioned to form drops of a predetermined volume and disposed for introducing said drops into an upper region of said drip chamber, and supply connector means for connection to a liquid supply and having an outlet passageway through which said liquid is supplied to said drip chamber, apparatus for coupling an outlet passageway of said supply connector means to said inlet connector to enable selective formation and introduction of drops of smaller volume than said predetermined volume into said upper region of drip chamber, said coupling apparatus comprising:
a resiliently flexible relatively large diameter first tube, a relatively small diameter second tube having a first end dimensioned to form said smaller volume drops and a second end, means for connecting opposite ends of said first tube respectively to said outlet passageway of said supply connector means and to said inlet connector, and means for supporting said second tube substantially coaxially within said first tube with said second end of said second tube disposed to receive liquid from said outlet passageway of said supply connector means and said first end of said second tube disposed to introduce said smaller volume drops into said upper region of said drip chamber substantially on an axis of said drop-forming opening of said inlet connector,
said second tube being sufficiently rigid relative to said first tube that when it is supported as aforesaid within said first tube, said first tube may be pinched shut against said second tube without pinching shut said second tube,
said first and second tubes having relative resistances to flow such that when respective inlet ends of said tubes confront a common flow of liquid and both of said tubes are open, the volumetric flow rate through said second tube is negligible in comparison with that through said first tube, whereby selection between the different volume drops may be made by pinching said first tube shut or leaving said first tube open in accordance with the desired drop size.

46. Coupling apparatus according to claim 45, wherein said connecting means comprises a pair of adapters.

47. Coupling apparatus according to claim 46, wherein said supporting means comprises a pair of fenestrated disks configured to fit said adapters and to retainably receive said second tube.

48. Coupling apparatus according to claim 45, further comprising clamping means for pinching said first tube shut against said second tube.

* * * * *